United States Patent
Beyar et al.

(10) Patent No.: US 6,378,525 B1
(45) Date of Patent: Apr. 30, 2002

(54) COMBINED CRYOTHERAPY AND HYPERTHERMIA METHOD FOR THE TREATMENT OF AIRWAY OBSTRUCTION OR PROSTRATE ENLARGEMENT

(75) Inventors: Motti Beyar, Herzliya; Ari DeRowe, Mosahav Salit, both of (IL)

(73) Assignee: American Medical Systems, Inc., Minnetonka, MN (US)

( * ) Notice: Subject to any disclaimer, the term of this patent is extended or adjusted under 35 U.S.C. 154(b) by 0 days.

(21) Appl. No.: 09/015,186

(22) Filed: Jan. 29, 1998

(51) Int. Cl.⁷ ............................................. A61B 19/00
(52) U.S. Cl. ........................................ 128/898; 606/23
(58) Field of Search ............................ 606/23, 24, 20, 606/21, 22, 106, 110; 128/898

(56) References Cited

U.S. PATENT DOCUMENTS

| | | | |
|---|---|---|---|
| 3,800,552 A | | 4/1974 | Sollami et al. |
| 3,913,581 A | | 10/1975 | Ritson et al. |
| 5,171,314 A | * | 12/1992 | Dulebohn .................. 606/113 |
| 5,201,741 A | * | 4/1993 | Dulebohn .................. 606/113 |
| 5,452,582 A | | 9/1995 | Longsworth |
| 5,514,131 A | * | 5/1996 | Edwards et al. ............ 606/45 |
| 5,522,870 A | | 6/1996 | Ben-Zion |
| 5,707,349 A | * | 1/1998 | Edwards ..................... 604/22 |
| 5,807,308 A | * | 9/1998 | Edwards ..................... 604/22 |
| 5,843,021 A | * | 12/1998 | Edwards et al. ............ 604/22 |
| 5,846,235 A | * | 12/1998 | Pasricha et al. ............ 606/23 |
| 5,988,171 A | * | 11/1999 | Sohn et al. ................ 128/848 |

* cited by examiner

Primary Examiner—Vincent Millin
Assistant Examiner—Kelly O'Hara
(74) Attorney, Agent, or Firm—Oppenheimer Wolff & Donnelly LLP

(57) ABSTRACT

A method of reducing tissue volume for treatment of airway obstruction, obstructive sleep apnea, snoring, prostate tumor, and other pathologies comprising: applying a cryoprobe with a diameter preferably less than about 2 mm and with a sharp tip to first freeze the affected interstitial tissue of the soft palate, base of the tongue, tonsils or adenoids, singularly or in combination, or to the prostate, or other tissue, and then applying the same cryoprobe to heat the treated tissue.

11 Claims, 2 Drawing Sheets

COMBINED CRYOTHERAPY AND HYPERTHERMIA METHOD FOR THE TREATMENT OF AIRWAY OBSTRUCTION OR PROSTRATE ENLARGEMENT

FIELD AND BACKGROUND OF THE INVENTION

The present invention relates to a method of reducing tissue volume by applying a unique cryoprobe. The invention is especially useful in reducing pharyngeal tissues, including tonsils and soft palate, in treating upper airway obstruction, such as exists in obstructive sleep apnea, and/or snoring, or in treating an enlarged prostate, and is described below with respect to such applications, but it will be appreciated that the invention could advantageously be used in other applications as well, such as, in treating abundant vascular tissue in the uterus, as found in menometrorrhagia, or in treating hypertrophic inferior turbinates in nasal obstruction.

Obstructive Sleep Apnea is of unknown etiology, but it is generally accepted that it results from the combination of a structurally small upper airway and a normal or abnormal loss of physiologic muscle tone during sleep. Patterns of pharyngeal narrowing and collapse suggest that 30–50% of patients with obstructive sleep apnea have obstruction at the level of the upper pharynx or in the retropalatal segment. This can be due to abundant tissue of the palate or tonsillar hypertrophy. An even higher percentage of snorers have the soft palate as the source of the vibrations of snoring.

Obstructive Sleep Apnea is a potentially life threatening disorder, which affects up to 2 to 4% of the adult population. Even when not life threatening, it is annoying to a bed mate. Obstructive Sleep Apnea is associated with snoring, which is believed to affect 20% of adults.

In the past, surgical treatments have been used to treat Obstructive Sleep Apnea. One treatment is by a surgical operation involving removal of the tonsils and soft palate (uvulopharyngeal palatoplasty). Another surgical treatment involves midline glossectomy. These surgical procedures often occur with general anesthesia, postoperative pain, bleeding risks, substantial recovery times and hospitalization. Recently, more minimal procedures have been introduced including laser resection and radio frequency volumetric reduction of the soft tissue palate.

OBJECTS AND BRIEF SUMMARY OF THE INVENTION

An object of the present invention is to provide a method of reducing tissue, which is particularly useful for treating tissue obstructions and enlargements, such as occurring in obstructive sleep apnea, by using a cryoprobe to first freeze and then sequentially heat the tissue. This invention has the advantage of being a minimally invasive procedure.

Another object of the present invention is to provide a method of reducing tissue with minimal bleeding, by using a cryoprobe to first freeze and ablate the tissue and then using the same or a different cryoprobe to heat and further ablate the tissue and to coagulate blood vessels. This invention also has the advantage of reducing or eliminating bleeding by coagulation resulting from thermoablation.

A further object of the present invention is to provide a method of reducing tissue by initially quickly freezing the tissue to reduce and locally destroy tissue and then heating the tissue to further reduce the tissue and to prevent or minimize bleeding. This method prevents or minimizes damage to mucous membranes and reduces pain and scarring.

According to the present invention, there is provided a method of reducing tissue, comprising: first applying a cryoprobe with a diameter preferably less than 2 mm and with a sharp tip to freeze the affected interstitial tissue of the soft palate, base of the tongue, tonsils or adenoids, singularly or in combination, and then applying a probe, preferably the same cryoprobe to heat to coagulate and/or ablate the treated tissue.

In one and the preferred described embodiment, interstitial ablation of the soft palate is performed by applying a cryoprobe with diameter preferably less than 2 mm and with a sharp tip to initially freeze the affected interstitial tissue of the soft palate, and then applying the same cryoprobe to heat the treated tissue to achieve further tissue removal, to achieve easier probe removal, to avoid sticking of tissue to the frozen probe surface and to coagulate the superficial vascular tissue surrounding the probe insertion site.

In a second described embodiment, interstitial ablation of the soft palate, base of the tongue, tonsils and/or adenoids is performed by applying a cryoprobe with a diameter preferably less than 2 mm and with a sharp tip to initially freeze the affected interstitial tissue, and, then, applying the same cryoprobe to heat the treated tissue to achieve further tissue removal, to achieve easier probe removal, to avoid sticking of tissue to the frozen probe surface and to coagulate the superficial vascular tissue surrounding the probe insertion site.

In a third embodiment, interstitial ablation of the soft palate, base of the tongue, tonsils and/or adenoids is performed by first applying a cryoprobe with a diameter preferably less than 2 mm and with a sharp tip to heat the affected interstitial tissue, and then applying the same cryoprobe to freeze the treated tissue to achieve further tissue removal.

In yet another embodiment, interstitial ablation of the soft palate, base of the tongue, tonsils and/or adenoids is performed by applying a cryoprobe with a diameter preferably less than 2 mm and with a sharp tip to only freeze the affected interstitial tissue.

In another embodiment, interstitial ablation of the soft palate, base of the tongue, tonsils and/or adenoids is performed by applying a cryoprobe with diameter preferably less than 2 mm and with a sharp tip to only heat the affected interstitial tissue.

In another embodiment, interstitial ablation of the ovopharynx is performed by applying a cryoprobe with a diameter preferably less than 2 mm and with a sharp tip to freeze the affected interstitial tissue.

In another embodiment, interstitial ablation of the ovopharynx is performed by applying a cryoprobe with a diameter preferably less than 2 mm and with a sharp tip to heat the affected interstitial tissue.

In another embodiment, interstitial ablation of the inferior turbinates of the nose is performed to relieve nasal obstruction by applying a cryoprobe with a diameter preferably less than 2 mm and with a sharp tip to initially freeze the affected interstitial tissue of the inferior turbinates and then applying the same cryoprobe to heat the treated tissue to achieve further tissue removal of the affected tissue. This is intended to relieve nasal obstruction.

In another embodiment, interstitial ablation of the prostate is performed by applying a cryoprobe with a diameter preferably less than 2 mm and with a sharp tip to initially freeze the affected interstitial tissue of the prostate, and applying the same cryoprobe to then heat the treated tissue to achieve further tissue removal, to achieve easier probe removal, to avoid sticking of tissue to the frozen probe surface and to coagulate the superficial vascular tissue surrounding the probe insertion site. The invention also contemplates applying a flexible cryoprobe of the described type for use in conjunction with a cystoscope.

In another embodiment, a thermoregulator is used to control the temperature of application of the cryoprobe.

The described methods of reducing tissue may also be used in other applications, for example, and not by limitation, in the medical treatment of menometrorrhagia.

Further features and advantages of the invention will be apparent from the description below.

BRIEF DESCRIPTION OF THE DRAWINGS

The invention is described, by way of example only, with reference to the accompanying drawings, where.

DETAILED DESCRIPTION OF THE DRAWINGS AND THE PREFERRED EMBODIMENTS

Figure 1:
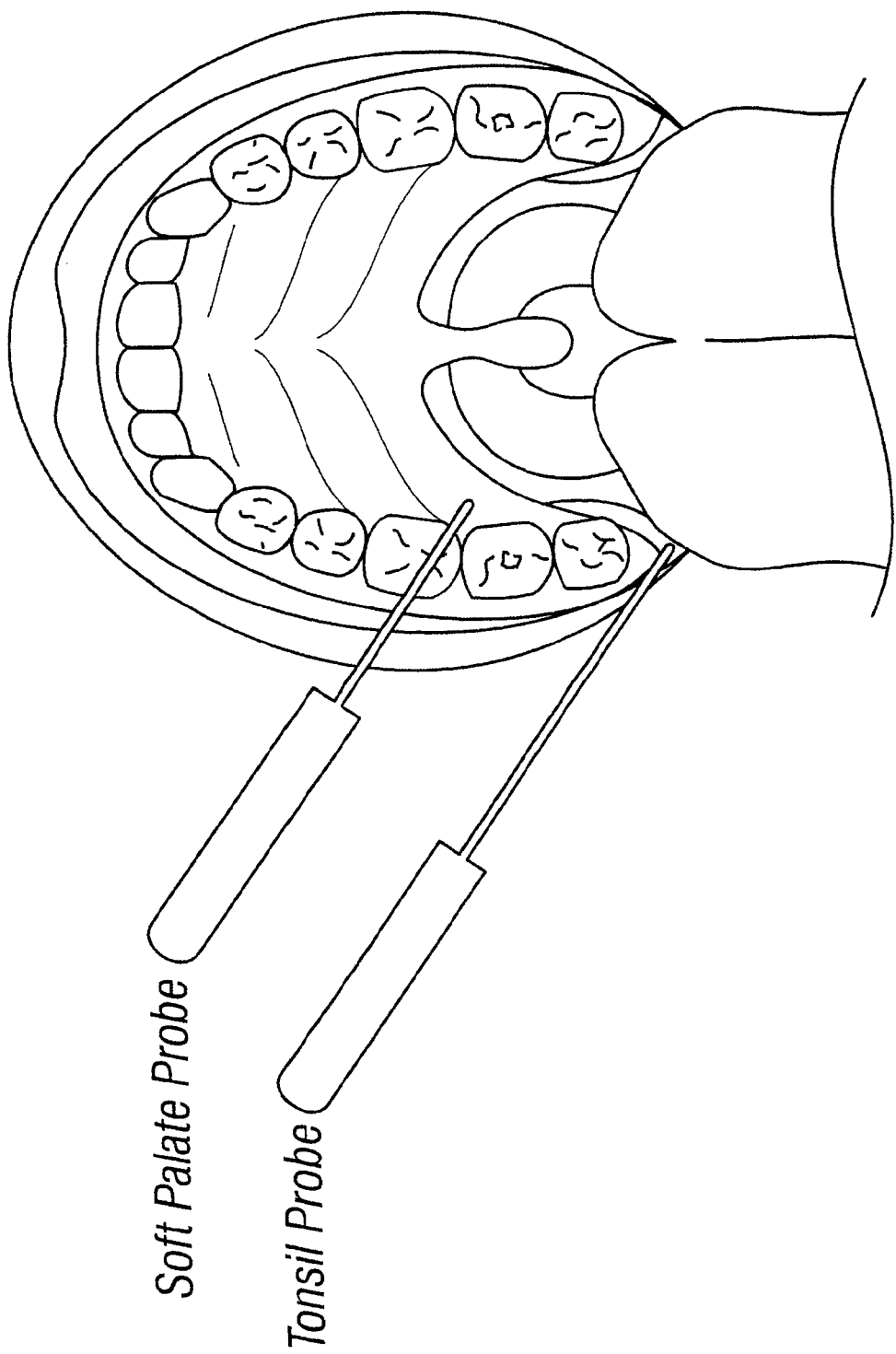
FIG. 1 is a front perspective view of a patient's mouth and illustrates one form of the method of reducing tissue, as applied to the soft palate in accordance with the present invention.

The method of reducing tissue, as illustrated in FIG. 1, comprises applying a cryoprobe, generally designated 1, with a diameter 2 (preferably less than 2 mm) and with a sharp tip 3, to initially freeze the affected interstitial tissue of the soft palate 4, and then, by applying the same cryoprobe to heat the treated tissue to achieve further tissue removal, to achieve easier probe removal, to avoid sticking of tissue to the frozen probe surface and to coagulate the superficial vascular tissue surrounding the probe insertion site.

Figure 2:
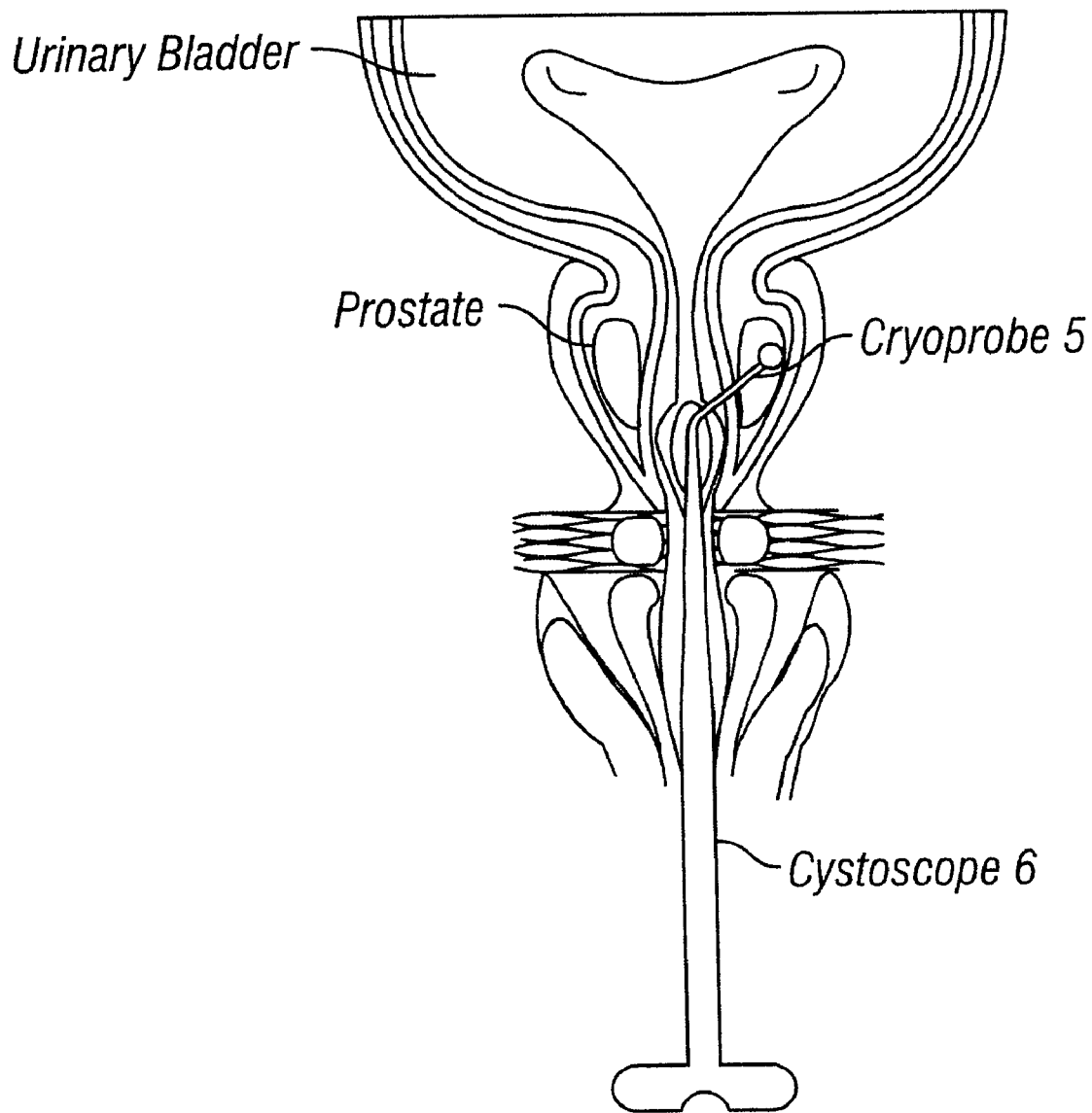
FIG. 2 is a sectional view of a patient's urinary tract and illustrates one form of the inventive method and apparatus for reducing an enlarged prostate.

FIG. 2 illustrates a variation of the basic and preferred method in which the cryoprobe 5 is flexible and used with a cystoscope 6.

While the invention has been described and illustrated in detail with respect to two particular applications, it will be appreciated that the described method of reducing tissue may be used in a wide variety of other medical applications, e.g., for treatment of menometrorrhagia; by reversing the steps so as to first heat and then freeze, by using the cryoprobe to freeze and then heat the endometrium of the uterus; by only heating or only freezing tissue, etc.

Many other variations and applications of the invention will be apparent to those of ordinary skill in the art.

We claim:

1. A method of reducing tissue comprising: locally changing the temperature of the tissue by application of both heat and freezing cold via a probe.

2. The method of reducing tissue according to claim 1, wherein changing the temperature further comprises:

applying the freezing cold to the tissue with the probe followed by applying the heat to the tissue with the probe.

3. The method of reducing tissue according to claim 2, wherein a single probe is used to apply the freezing cold and the heat to the tissue.

4. The method of reducing tissue according to claim 2, wherein the freezing cold and heat is applied to a patient's prostate.

5. The method of reducing tissue according to claim 2, said tissue including interstitial tissue of a patient's prostate, further comprising:

inserting a cystoscope into an enlarged prostate, said cystoscope having a working channel;

inserting the probe through the cystoscope working channel into the enlarged prostate, wherein the probe is flexible;

freezing interstitial tissue of the enlarged prostate; and heating the interstitial tissue of the enlarged prostate.

6. The method of reducing tissue according to claim 1, wherein a single probe is used to apply the freezing cold and the heat to the tissue.

7. The method of reducing tissue according to claim 1, wherein the freezing cold and the heat is applied to a patient's prostate.

8. The method of reducing tissue according to claim 1, said tissue including a patient's prostate, wherein changing the temperature comprises:

freezing the prostate with the probe followed by heating the prostate with the probe, wherein said method treats prostate enlargement.

9. The method of reducing tissue according to claim 1, said tissue including interstitial tissue of a patient's prostate, further comprising:

inserting the probe into a prostate;

freezing the interstitial tissue of the prostate; and heating the interstitial tissue of the prostate.

10. The method of reducing tissue according to claim 1, said tissue including interstitial tissue of a patient's prostate, further comprising:

inserting the probe into an enlarged prostate;

freezing the interstitial tissue of the enlarged prostate; and heating the interstitial tissue of the enlarged prostate, wherein the freezing and heating reduces the interstitial tissue of the enlarged prostate.

11. The method of reducing tissue according to claim 1, wherein the probe is a flexible probe.

* * * * *